United States Patent
Keep et al.

(10) Patent No.: US 7,629,801 B2
(45) Date of Patent: Dec. 8, 2009

(54) SENSING SYSTEM FOR USE IN DETECTING A SURFACE CONDITION OF A ROADWAY SURFACE

(75) Inventors: Dale Keep, Walla Walla, WA (US); Lance Doyle, Walla Walla, WA (US)

(73) Assignee: Zydax, LLC, Walla Walla, WA (US)

( * ) Notice: Subject to any disclaimer, the term of this patent is extended or adjusted under 35 U.S.C. 154(b) by 0 days.

(21) Appl. No.: 11/487,157

(22) Filed: Jul. 13, 2006

(65) Prior Publication Data

US 2007/0145985 A1 Jun. 28, 2007

Related U.S. Application Data

(60) Provisional application No. 60/699,931, filed on Jul. 14, 2005.

(51) Int. Cl.
 G01R 27/08 (2006.01)
 G01W 1/00 (2006.01)
(52) U.S. Cl. .................. 324/694; 324/691; 73/170.17
(58) Field of Classification Search .......... 324/694
See application file for complete search history.

(56) References Cited

U.S. PATENT DOCUMENTS

| | | | |
|---|---|---|---|
| 3,891,979 A | 6/1975 | Braun et al. | |
| 4,745,803 A * | 5/1988 | Haavasoja | 73/170.26 |
| 4,926,163 A | 5/1990 | Beebe | |
| 5,745,051 A | 4/1998 | Doherty et al. | |
| 5,757,197 A * | 5/1998 | O'Neill | 324/696 |
| 6,239,601 B1 * | 5/2001 | Weinstein | 324/662 |
| 6,300,865 B1 | 10/2001 | Fechner et al. | |
| 6,441,748 B1 | 8/2002 | Takagi et al. | |
| 6,662,099 B2 | 12/2003 | Knaian et al. | |
| 6,977,597 B2 | 12/2005 | Doherty | |
| 7,164,365 B2 | 1/2007 | Doherty et al. | |
| 7,187,926 B1 * | 3/2007 | Henkel | 455/428 |
| 7,358,858 B2 | 4/2008 | Ozawa et al. | |
| 7,421,894 B2 * | 9/2008 | Keep et al. | 73/170.19 |
| 2004/0124856 A1 * | 7/2004 | Venter et al. | 324/664 |
| 2005/0252285 A1 * | 11/2005 | Boehm | 73/146 |

* cited by examiner

Primary Examiner—Jeff Natalini
(74) Attorney, Agent, or Firm—Perkins Coie LLP (57) ABSTRACT

The present invention is generally directed toward sensors and associated methods, including surface condition sensors. For example, in certain embodiments sensor can be configured to sense the surface conditions on a road surface and/or an airport surface. One aspect of the invention is directed wet/dry sensors. Other aspects of the invention are directed toward conductivity sensors. Still other aspects of the invention are directed toward sensor packages that include a combination of active and passive sensor technology. Yet other aspects of the invention are directed toward communication systems and methods associated with various sensors.

8 Claims, 11 Drawing Sheets

| Pin 31 | Pin 32 | Pin 33 | Pin 34 | Signal |
|---|---|---|---|---|
| 0 | 0 | 0 | 0 | None |
| 0 | 0 | 0 | 1 | 9 (E1) |
| 0 | 0 | 1 | 0 | 10 (E2) |
| 0 | 0 | 1 | 1 | 11 (E3) |
| 0 | 1 | 0 | 0 | 12 (E4) |
| 0 | 1 | 0 | 1 | 13 (E5) |
| 0 | 1 | 1 | 0 | 14 (E6) |
| 0 | 1 | 1 | 1 | 15 (E7) |
| 1 | 0 | 0 | 0 | 16 (E8) |
| 1 | 0 | 0 | 1 | 17 (E9) |
| 1 | 0 | 1 | 0 | REF A (C14) |
| 1 | 0 | 1 | 1 | REF B (C15) |
| 1 | 1 | 0 | 0 | Internal Oscillator |
| 1 | 1 | 0 | 1 | Internal Oscillator after internal 22K |
| 1 | 1 | 1 | 0 | Internal Ground |
| 1 | 1 | 1 | 1 | Reserved |

| Pin 5 | Pin 6 | Pin 7 | Gain |
|---|---|---|---|
| 0 | 0 | 0 | 0 |
| 1 | 0 | 0 | -1 |
| 0 | 1 | 0 | -2 |
| 1 | 1 | 0 | -5 |
| 0 | 0 | 1 | -10 |
| 1 | 0 | 1 | -20 |
| 0 | 1 | 1 | -50 |
| 1 | 1 | 1 | -100 |

SENSING SYSTEM FOR USE IN DETECTING A SURFACE CONDITION OF A ROADWAY SURFACE

CROSS REFERENCE TO RELATED APPLICATIONS

This patent application claims priority to U.S. Provisional Patent Application No. 60/699,931, entitled "ROADWAY SENSOR SYSTEM", filed Jul. 14, 2005, which is incorporated herein in its entirety by reference thereto.

TECHNICAL FIELD

The following disclosure relates generally to sensors and associated methods, including surface condition sensors.

BACKGROUND

Surface conditions of a road or runway can change rapidly with changes in weather and other environmental conditions. These changes in surface conditions can greatly affect the operation and safety of vehicles operating on these surfaces. For example, a build up of moisture, contaminants, or other surface coverings on a road can greatly affect the stopping distance of a motor vehicle driven at a selected speed. If the surface conditions are known, the vehicle operator can take the surface conditions into consideration when operating the vehicle. For example, the vehicle operator can reduce speed and increase following distances when driving on a wet road. Additionally, when surface conditions are known, maintenance crews may be able to take actions to improve the surface conditions so that operating safety can be increased. Accordingly, it can be important to track changes in surface conditions of a road or runway in a timely manner and to provide this information to vehicle operators, maintenance crews, and the like.

DETAILED DESCRIPTION

The present invention describes sensors and associated methods, including surface condition sensors. Several specific embodiments are set forth in the following description and in FIGS. 1-14 to provide a thorough understanding of certain embodiments of the invention. One skilled in the art, however, will understand that the present invention may be practiced without several of the specific features explained in the following description.

A. Introduction

Certain aspects of the invention includes a device used to determine weather related pavement or concrete conditions such as on a highway, runway, parking lot or other paved surfaces. A block of electrically insulated material is embedded in the pathway in a location that substantially represents the conditions of the area to be monitored. An intelligent Active/Passive sensor that detects the presence of water or liquid anti-icing chemical, presence of ice, a freeze point of the liquid (if any), depth of moisture, surface temperature, pavement temperature, and the ability to communicate directly to the end user/customer or to an intermediate data logging computer such as a Remote Processing Unit (RPU) or Central Processing Unit (CPU) as used in a Roadway Weather Information System (RWIS) using a published open protocol encapsulated by the electrically insulating material. Communications to the device can be via hardwired connections to a computer, via landline modem, via cellular modem or via any other technology that results in a "virtual serial port" between the sensor and the logging computer. The device is configured with a unique address that allows it to be attached to a signal bus with other devices as long as all the devices can communicate and do not interfere with each others operation. The presence of moisture is detected by using two or more electrodes that are driven with a low power sine wave. The rectified, filtered signal is then processed to determine if moisture is present. Conductivity is determined using an Electromagnetic Induction sensing method. Conductivity along with temperature can be used to determine freeze point, depth of moisture, and presence of ice.

Certain aspects of the invention are directed toward roadway sensor data collections methods. For example, sensors typically utilized in Roadway Weather Information Systems (RWIS) and other areas such as airport systems have historically required a layering of communications systems with mostly closed protocols to make the data from the sensors available to the consumer (end user). As a result of the layering of equipment and software it has historically been very expensive and required the expensive assistance of the sensor provider for changes, repairs or changes to the proprietary system. By utilizing truly intelligent sensors with open protocol communications, the ability to communicate directly with the end user is provided and at a very much-reduced price. Additionally, these intelligent sensors can be added to any system containing Remote Processing Units (RPU) and/ or Centrally Located Processing Units (CPU). With this approach, sensor data can now be delivered to the consumer at a lower cost and provides the consumer the sensor data to use at their discretion without the assistance of the sensor provider.

Selected aspects are directed toward wet/dry sensor(s). For example, the Wet/Dry sensor technology utilized in the intelligent sensor provides a much higher resolution and accuracy than technologies currently utilized. The intelligent sensor can detect the presence of even the smallest amount of moisture on a surface. This technology can also accurately report dry surfaces even in the presence of dry salt crystals (commonly used deicer product) where false wet readings are most often reported with the use of current technology. Certain embodiments of the intelligent sensor and this technology have the ability to provide wet to dry transitions data, and current surface conditions at 3 or more different levels, including wet, dry, and trace.

Additionally, selected embodiments of the intelligent sensor and this technology provide the ability to set and adjust thresholds to enable very accurate reporting of the three surface conditions and transitions between them. In certain embodiments, threshold adjustments can be made to provide the wet, dry or trace information to accommodate the needs of any consumer or location. Once the thresholds are set, the intelligent sensor can then apply automatic temperature compensation to provide data currently unavailable in a single package.

Certain aspects are directed toward conductivity sensor(s). For example, the conductivity sensor can provide a rugged durable method of determining the conductivity of moisture present on a surface to determine the presence (or lack of) of anti-icing chemicals and their concentration if present. From the concentration reading, the intelligent sensor can then utilizes the built in "SET UP" data and look up tables to determine the freeze point of the moisture on the surface. In selected embodiments, this technology provides a signal with no DC content, which eliminates concerns of galvanic corrosion or plating of the electrodes. Galvanic corrosion of electrodes can be a concern with the some technologies currently utilized. Corrosion of electrodes can cause the accuracy of the data to deteriorate and can eventually cause the sensor to quit working all together.

Selected aspects of the invention are directed toward combining active and passive highway surface sensor(s) in one package. For example, certain embodiments both active and passive sensors, combined in a single package, can be used to determine a freeze point of moisture or liquid that may be present on a highway, runway or other surface. The combining of the active and passive abilities into an intelligent sensor to determine the freeze point of moisture that may be present provides the ability to report very accurate data. It also simplifies installation by requiring less cutting of surfaces and typical reduces the number and/or size of the cables that need to be installed to support the multiple sensors. This combining of abilities into a single intelligent sensor package also simplifies, procurement, reduces purchase price, (when compared to equal performance and abilities) sensor maintenance requirements, and overall operational costs.

Historically, data from sensors monitoring the weather conditions on highways, airports and other surfaces have required the use of a local data collection computer known as a Remote Processor Unit (RPU) located near the sensor(s) and a Central Processor Unit (CPU) to make the data available to the end user. In selected embodiments, by utilizing intelligent sensors with remote communications ability, and by providing (e.g., free) a software package to collect that data, the RPU and CPU can be eliminated. The addition of the remote communications capability does not prevent the use of an RPU and/or CPU allowing the intelligent sensor with its open protocol to be placed into new or existing systems. An intelligent sensor possessing both the remote communications and local serial communications capability may be connected to communicate to an RPU, a CPU or directly to a consumer's computer. The data from the intelligent sensor(s) may be processed by the RPU, CPU or if desired delivered directly to the consumer in a user friendly easy to read format. All data strings can be open protocol. The use of open and published protocol can allow for easy integration of the intelligent sensor(s) into the any data collection system the user desires. In addition, in selected embodiments, layered levels of communications can allow a single access point to external communications and simplify the installation and reduce costs of installation and ongoing costs. In certain embodiments, supplying a freely distributable data collection program that runs on a standard computer with Microsoft Windows (2000 or newer), Linux, or UNIX, operating systems gives the user the flexibility to implement an economical, flexible sensor network that meets their needs.

Figure 6:
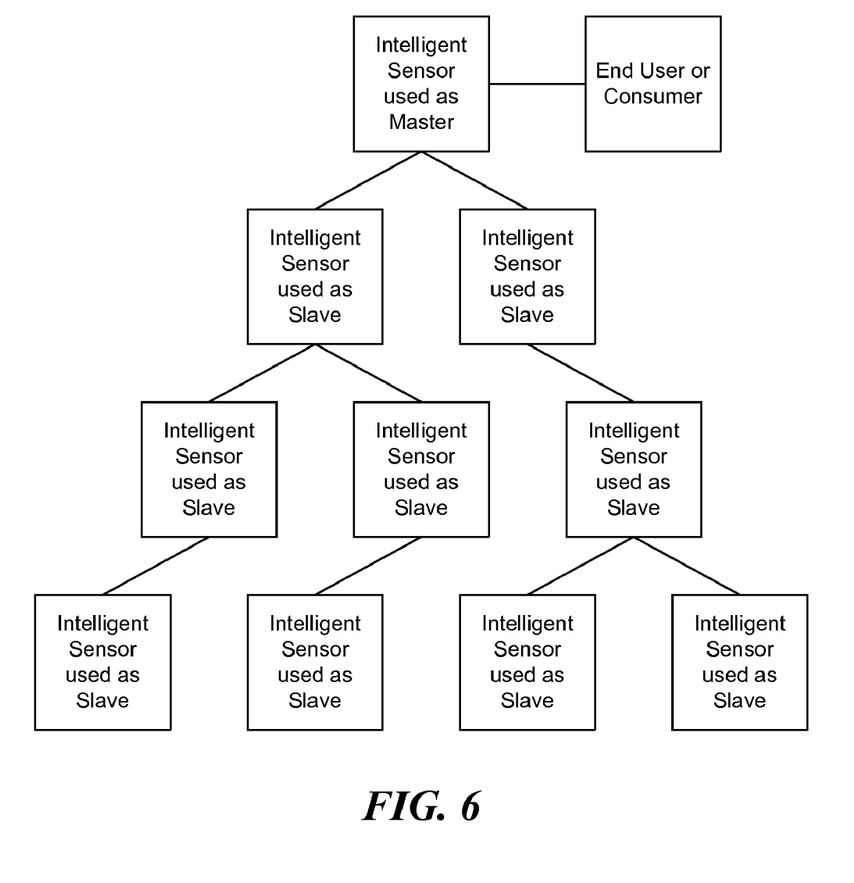
FIG. 6 is a partially schematic illustration of sensor(s) utilized in a master-slave relationship communicating through the master to the consumer in accordance with other embodiments of the invention
Figure 7:
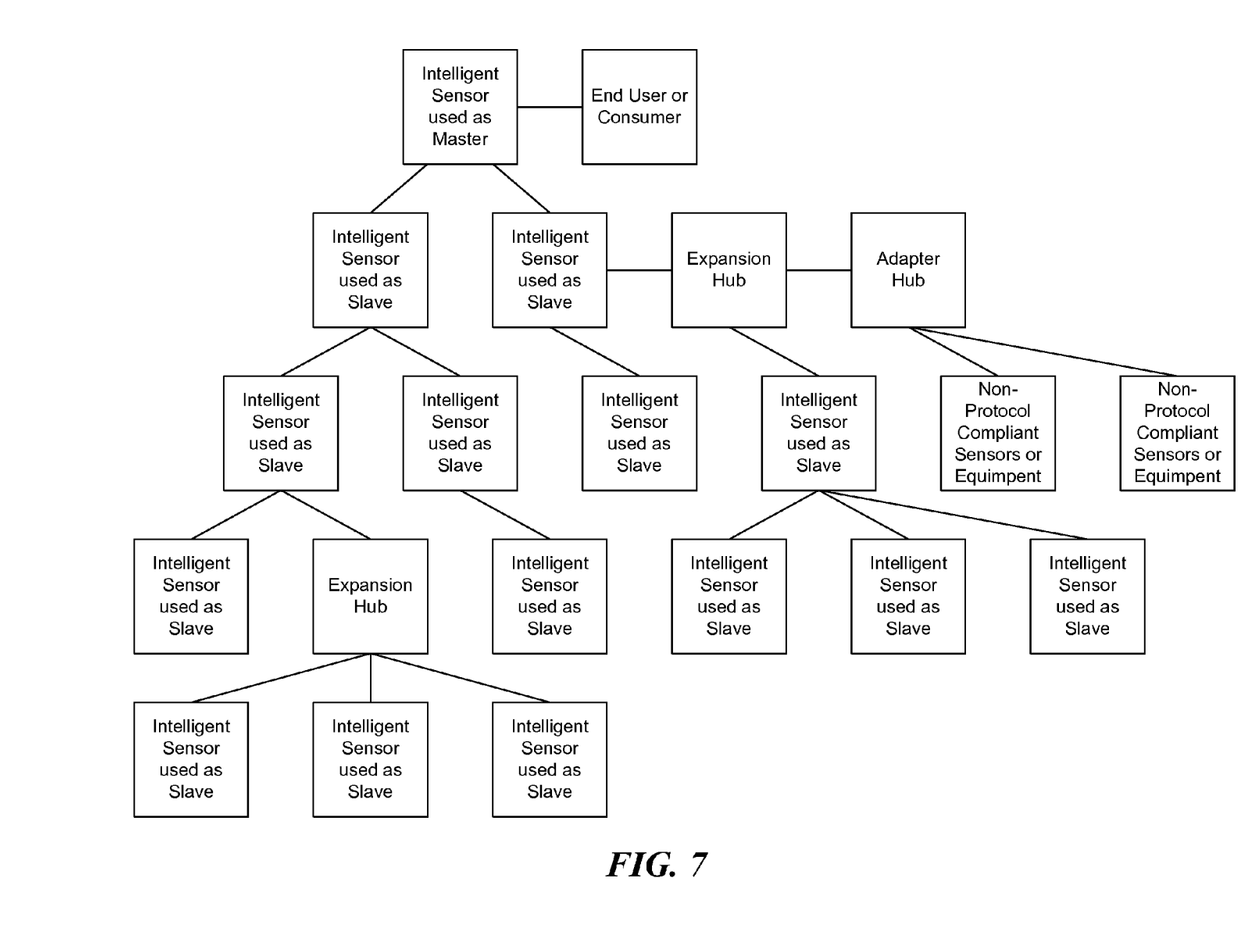
FIG. 7 is a partially schematic illustration of Sensor(s) utilized in a master-slave using expansion hubs and adapter hubs to allow use of non-protocol compliant sensors or equipment within the communications network in accordance with selected embodiments of the invention.
Figure 8:
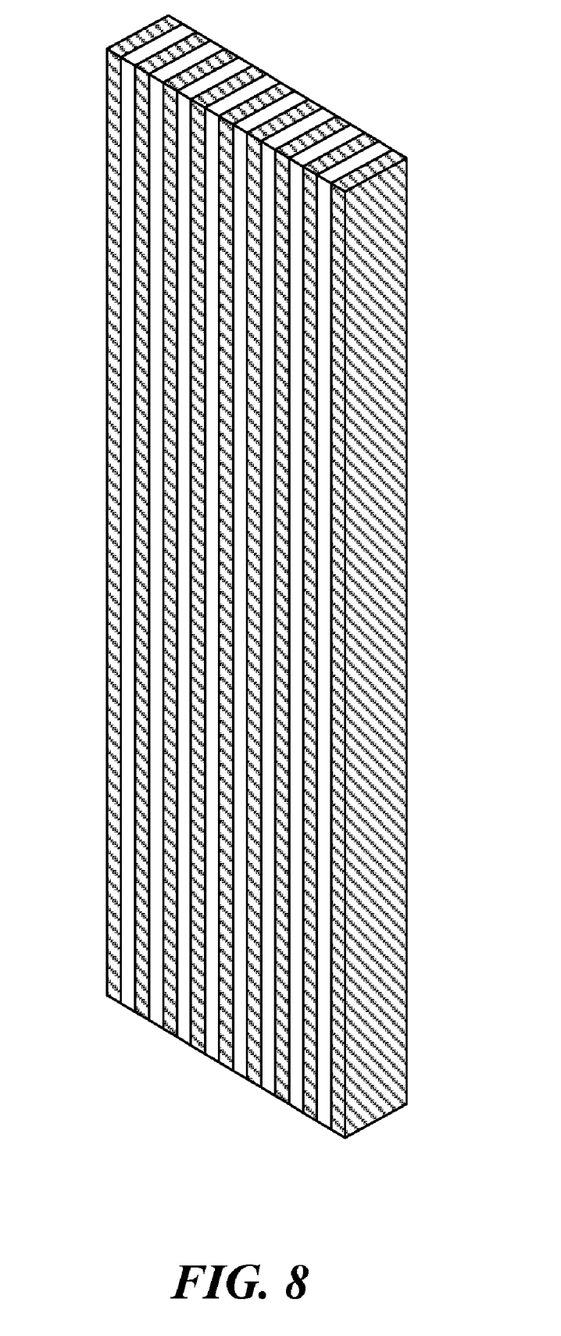
FIG. 8 is a partially schematic illustration of a wet/dry electrode displaying lamination and stacked components in accordance with certain embodiments of the invention.
Figure 9:
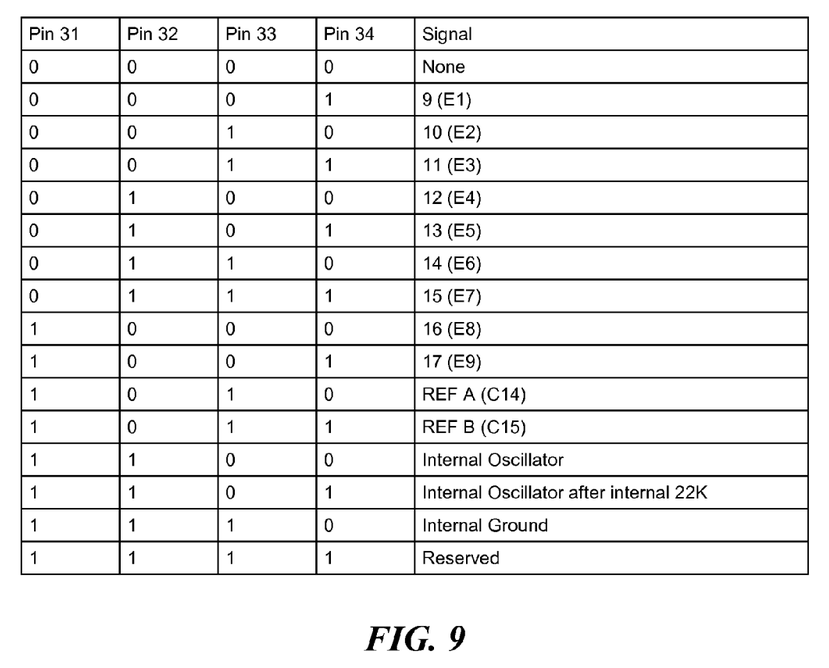
FIG. 9 is a table of wet/dry electrode selections in accordance with selected embodiments of the invention.

In selected embodiments, sensors can be utilized in a master-slave relationship and can communicate in various configurations (e.g., configurations shown in FIGS. 1 through 4). FIG. 6 represents another embodiment where multiple layers of sensors can be extended indefinitely (e.g., with the only limitations being communications bandwidth and the processing power of the master sensor). FIG. 7 shows another embodiment that uses adapter hubs to allow integration of non-protocol compliant devices into the communications network. For example, the adapter hubs can translate the information from non-protocol compliant devices. Regardless of the number of layers or slave sensors utilized, communications and data gathering from all sensors in the "Group" of all sensors can be controlled by the intelligent master sensor. Each "Group" of sensors is unique and identified by the address of the master sensor. The combination of the master sensor's address and the unique ID of each slave sensor connected to the master sensor identify each slave sensor(s) under that intelligent master sensor and the source of all data reported from the group of sensors.

The mobilized public has the need to have access to safe traveling conditions in all seasons and weather conditions. For example, as weather conditions change, traveled surfaces are not always bare. With accurate information on current surface conditions (at times combined with a weather forecast), maintenance departments can perform tasks to return the surface conditions to a bare surface. If a bare surface is not possible due to current conditions, knowing the current status can provide the information necessary to implement a plan to at least improve them until a bare surface can be achieved.

One of the parameters that can affect the safety of a traveling surface is the presence of water or moisture, especially at temperatures at and below the freeze point of water (32° Fahrenheit (F), 0° Celsius (C)). Moisture from rain, fog, snow, and sleet can all have a negative affect to safety if not monitored. In certain embodiments, measuring and reporting an accurate assessment of the presence of moisture along with surface temperature, pavement temperature, subsurface temperature, and air temperatures provides the data utilized by maintenance crews to predict near future surface conditions and the best way to deal with current conditions. With its open protocol, the data from the intelligent sensor(s) in selected embodiments can also be utilized in computerized models designed to forecast weather and/or surface conditions.

In addition to addressing concerns about potential icing of surfaces, many locations experience long dry periods with no rain. During this time, oils and other contamination build up on the surface of the highway. Except in extreme contamination such as spills, the coefficient of friction remains high while the traveling surface remains dry. When water is introduced to the surface (e.g., by rain, dew, or fog), the coefficient of friction most often drops dramatically increasing the potential for accidents due to decreases in traction, braking effectiveness, and the like. Accordingly, accurately knowing when even small amounts of moistures are present can provide maintenance personnel with the opportunity to implement a number of options to deal with the conditions at hand.

Selected embodiments of the invention provide for economical and accurate method of determining whether there is moisture present on a surface.

(1) Conductivity Sensor

When a surface is at, near, or below the freeze point of water (32° F., 0° C.) and moisture is present, ice can form (e.g., assuming lack of a deicer Chemical) presenting hazardous conditions. In selected embodiments, the conductivity of the moisture or water that may be present on a surface can provide indications of the presence of water and the amount of impurities (deicer chemicals) in the water. Often, deicer chemicals are applied to the water to keep it from freezing or to ice to melt it if ice is present. In either case, a successful deicer application depresses the freeze point of water to provide a wet surface. There is a relationship between the conductivity of the moisture present on the surface and the amount of the deicer or freeze point depressant present. A conductivity sensor can provide an indication of the freeze point of the moisture on the surface by sensing the variations in conductivity or amount of deicer chemical present. Water has a higher conductivity than ice and thus the conductivity sensor can also be used to indicate the formation of ice. In certain embodiments, this is one method of implementing "Passive Freeze Point Detection".

In selected embodiments of the invention, encapsulated toroids include two conductive leads that extend away from the encapsulant of the encapsulated toroids and are configured to be placed on or proximate to two distinct points on a surface (e.g., a roadway, a runway, concrete, pavement, or the like). In certain embodiments, the two conductive leads can be coupled together by a body portion that extends through the centers of the encapsulated toroids. Accordingly, even small amounts of moisture present on the surface can provide an electrical connection between the two points, completing the conductive path. With this approach the sensor surface senses (and can report) the conductivity of the moisture present (if any) by reading the conditions as present on the surrounding surface. The intelligent sensor in this embodiment can also have the advantage of galvanic isolation and physical isolation from the supporting electronics.

In selected embodiments the temperature of the points (e.g., electrodes) described can be changed, thereby heating or cooling any material present on the surface. In certain embodiments, this can be accomplished by the use of a Peltier device, thereby forming an "Active Freeze Point Detection Sensor." This approach can allow both passive (conductive reading only) and active (heating and/or cooling) sensor capabilities to be incorporated into a single sensor or sensor package.

(2) Active and Passive Surface Sensor in One Package

In certain embodiments, the active sensor or sensor capability can actively modify the temperature of a portion of sensor and/or surface in an attempt to freeze any moisture present and/or melt any ice present. By cooling the moisture present on the surface and detecting when it freezes, the freeze point of the moisture can be determined. Alternatively, heat can be applied to existing ice the conditions at which it melts or changes to water can be sensed.

In selected embodiments, the passive sensor or sensor capability the concentration of chemical(s) present can be usually be determined by the conductivity reading and the freeze point reported when the chemical(s) present in the moisture or ice are known. However, in some cases, contamination and the constituents of the freeze point depressant utilized can affect the accuracy of this process and the data reported. In certain embodiments with the active sensor or sensor capability, the makeup of the moisture on the surface does not matter. The actual freeze point of the material is measured and reported. This measurement includes the affect or lack of effect, of any contaminants that could be present on the surface. In selected embodiments, accurate information on surface and pavement temperatures combined with the freeze point of the moisture or ice present on the surface can be used to determine the correct actions to take to maintain or regain a safe travel or other surfaces.

In certain embodiments of the invention combine the two sensor capabilities into a single encapsulated package with a single cable providing all communications to a data logger or RPU. This approach can require less cutting of the surface during installation of the sensor, simplifying the install, reducing install time, reducing installation costs, and reducing installation materials. Additionally, this approach can be less intrusive into the surface where it is to be installed, which can be important on bridge deck installations and which can reduce the chances of installation failures do to the small number of components required to collect and communicate data. Furthermore, in selected embodiments the use of an embedded microcontoller, multiple temperature sensors and the combination active-passive intelligent sensor provides the ability to utilize active sensor technology circuits without materially affecting the measurement of the surface temperature or the passive sensor capabilities.

B. Roadway Sensor Data Collections Method

Historically, data from sensors monitoring the weather conditions on highways, airports and other surfaces have required the use of a local data collection computer known as a Remote Processor Unit (RPU) located near the sensor(s) and a Central Processor Unit (CPU) to make the data available to the end user. In selected embodiments, by utilizing intelligent sensors with remote communications ability, and by providing (e.g., free) a software package to collect that data, the RPU and CPU can be eliminated. In certain embodiments, the addition of the remote communications capability does not prevent the use of an RPU and/or CPU allowing the intelligent sensor (e.g., with open protocol) to be placed into new or existing systems. For example, an intelligent sensor possessing both the remote communications and local serial communications capability may be connected to communicate to an RPU, a CPU or directly to the consumer's computer. The data from the intelligent sensor(s) may be processed by the RPU, CPU or if desired delivered directly to the consumer in a user friendly easy to read format. In selected embodiments, all data strings can be open protocol. The use of open and published protocol can allow for easy integration of the intelligent sensor(s) into various data collection system the user might desire to use.

For example, in certain embodiments supplying a freely distributable data collection program that runs on a standard computer with Microsoft Windows (2000 or newer), Linux, or UNIX, operating systems gives the user the flexibility to implement an economical, flexible sensor network that meets their needs. The following FIGS. 1-7 reflect those abilities.

Figure 1:
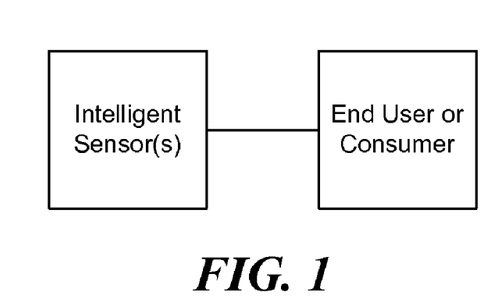
FIG. 1 is a partially schematic illustration of sensor(s) to consumer communications in accordance with certain embodiments of the invention.
Figure 2:
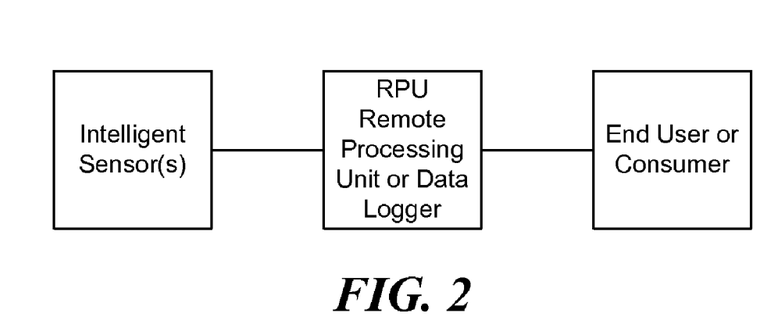
FIG. 2 is a partially schematic illustration of sensor(s) to remote processor unit (RPU) to consumer communications in accordance with selected embodiments of the invention.
Figure 3:
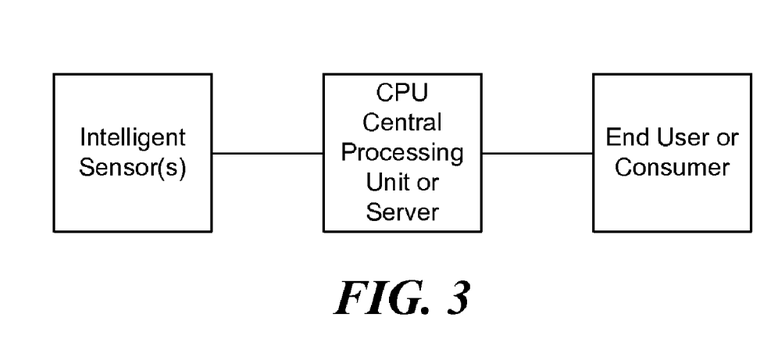
FIG. 3 is a partially schematic illustration of sensor(s) to central processing unit (CPU) to consumer communications in accordance with certain embodiments of the invention.
Figure 4:
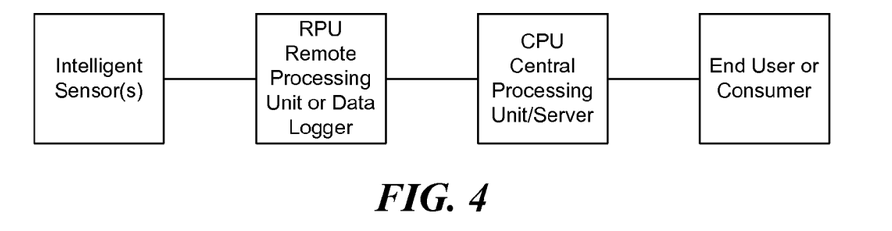
FIG. 4 is a partially schematic illustration of sensor(s) to RPU to CPU to consumer communications in accordance with selected embodiments of the invention.
Figure 5:
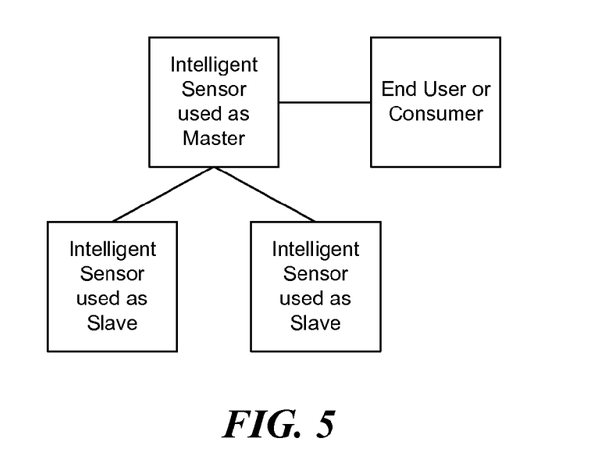
FIG. 5 is a partially schematic illustration of sensor(s) utilized in a master-slave relationship communicating through the master to the consumer in accordance with certain embodiments of the invention.

In selected embodiments, intelligent sensors can utilize a master-slave relationship and can communicate in configurations similar to those shown in FIGS. 5-7. In FIG. 5 there is only a single layer of slave sensors. In certain embodiments, the layer of slave sensors can be extended indefinitely with the only limitations being bandwidth and processing power of the master sensor. In selected embodiments, regardless of the number of layers or slave sensors utilized, the intelligent master sensor controls communications and data gathering from all sensors in the "group" of sensors. Each "group" of sensors can be unique and identified by the address of the master sensor. The combination of the master sensor's address and the unique ID of each slave sensor connected to the master sensor can be used to identify the slave sensor(s) under that intelligent master sensor and the source of all data reported from the group of sensors.

C. Wet/Dry Sensor

Selected embodiments of the invention can be implemented using a Freescale Semiconductor MC33794 Electric Field Imaging Device (e.g., integrated circuit U1) to drive Wet/Dry sensing electrodes. For example, this circuitry can be used measure effective conductivity of materials on the surface of the sensor. In certain embodiments, there is no attempt to convert the measured value to a standard measurement value. In the illustrated embodiment this circuitry drives nine electrodes sequentially.

In the illustrated embodiment, the electrodes are built of a lamination of polymer-impregnated graphite for the conductive layers and methylmethacrylate for the insulating layers. The electrodes are laminated and cut to fit into an edge card connector. This allows for electrical connections and mechanical location of the electrode. In selected embodiments, the materials for the electrodes are chemically resistant to common liquids and deicing compounds; physically tough to withstand the abuse that they might be subjected to on a highway, airport environment (e.g., runway, taxiways, and the like), or other surfaces; and resistant to ultraviolet light.

In the illustrated embodiment, the integrated circuit generates a low radio frequency sine wave with very low harmonic content. The circuit applies the AC coupled sine wave onto one electrode at a time while the other eight electrodes are grounded. The circuit monitors the driven electrode and delivers a rectified and filtered voltage level to an analog to digital converter. The voltage level is stored and the next electrode in sequence is stimulated and measured until all electrodes have been measured. The values are measured against a temperature compensated table to determine if the value for each electrode is representative of a dry surface, a surface with a trace of moisture or a wet surface. In the illustrated embodiment, the lowest values from any four electrodes are used to determine the surface condition.

In certain embodiments, an absolute threshold value is not set for the Dry/Trace or Trace/Wet conditions as many variables determine the value. These variables can include the length of cables used, the size of the wet/dry electrodes, the analog to digital converter circuit used, and the materials used for the electrodes.

In one embodiment, the typical threshold values for Dry/Trace are 30,000 at 20° C. and are 28,000 at 20° C. for Trace/Wet. The temperature coefficient is −100 counts per ° C. for both thresholds. The value of the temperature coefficient is linear and the slope is −100. As such, for each degree Celsius the temperature raises, a value of 100 is subtracted from the base threshold setting. For each degree Celsius the temperature drops, a value of 100 is added to the base threshold setting. The formula for this embodiment is:

$$Y=MX+B \text{ Where}$$

Y equals the adjusted threshold value
X equals the current surface Temperature
B equals the threshold value at zero (0) degrees Celsius.

In selected embodiments, a state machine can be used to control the timing and sequencing of the electrode stimulation. Due to the time constant of the filter components and the input capacitance of the AD converter circuit, in certain embodiments the sequencer can remain or dwell at each electrode for a sufficient time to allow the voltage to settle.

Figure 12:
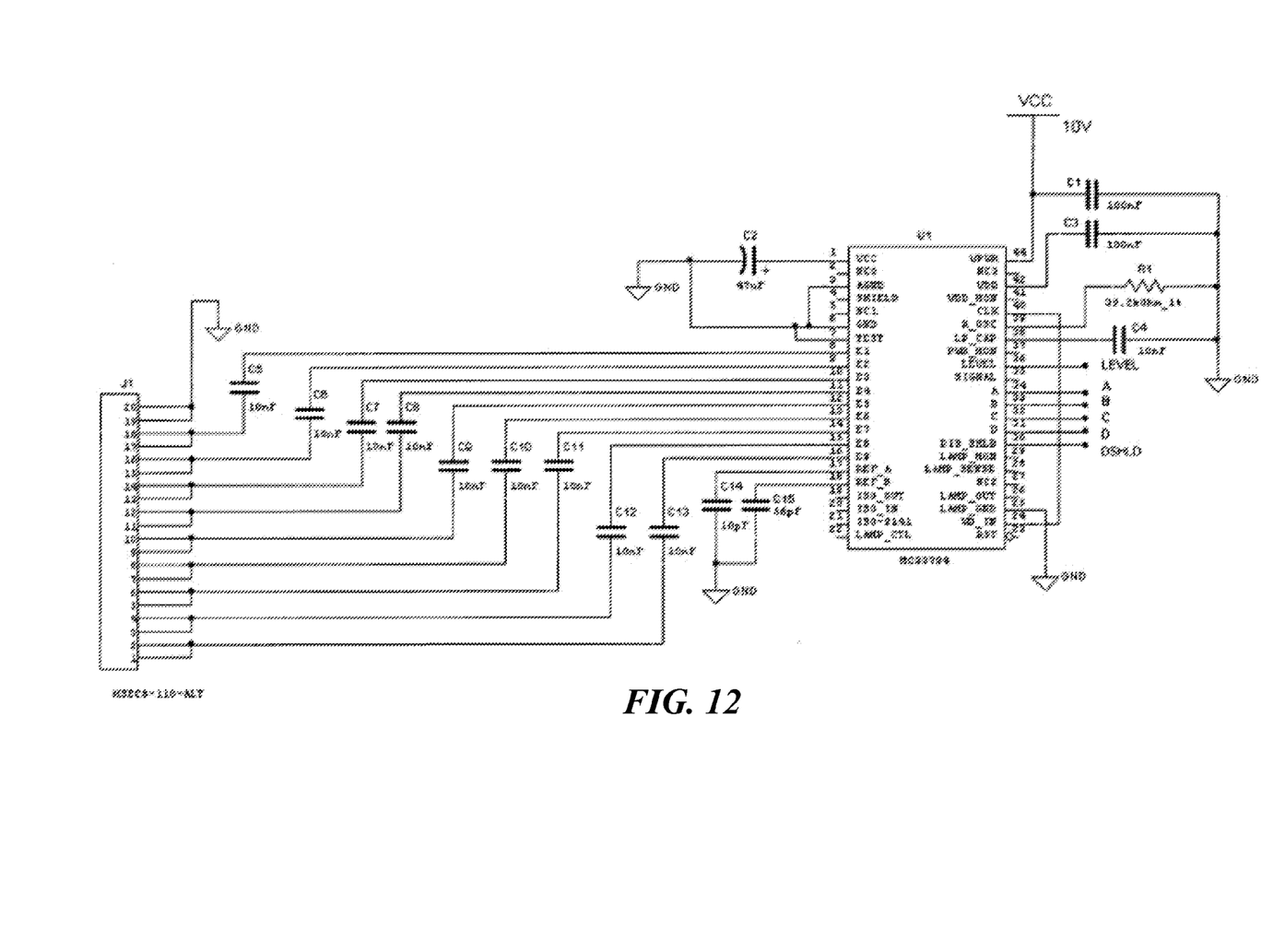
FIG. 12 is a partially schematic illustration of an Efield circuit in accordance with certain embodiments of the invention.
Figure 13:
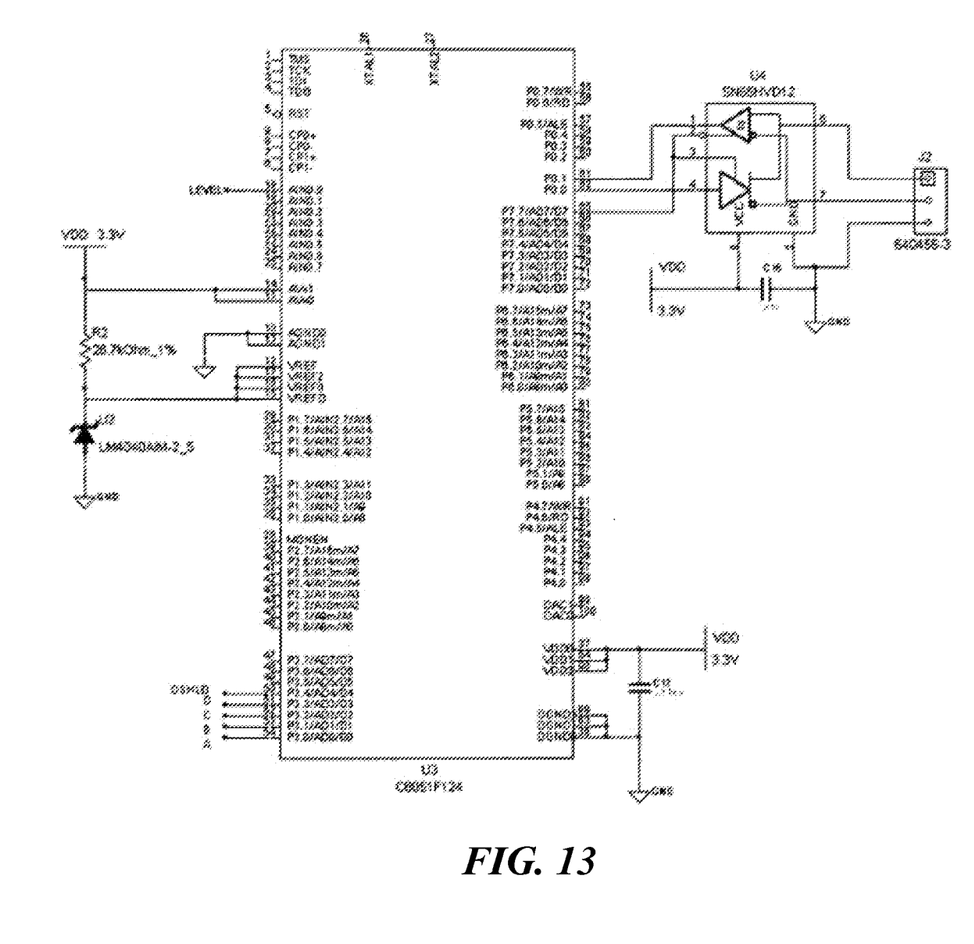
FIG. 13 is a partially schematic illustration of wet/dry sensor controller and communications in accordance with selected embodiments of the invention.

Turning now to FIG. 12 and FIG. 13. FIG. 12 shows the electronic components of the Wet/Dry sensing method in accordance with certain embodiments of the invention. In the illustrated embodiment, J1 is an edge card connector that provides the method of making the electrical connection to the conductive graphite elements of the Wet/Dry Electrode. The connector used in this embodiment is the Samtec HSEC8-110-01-S-DV-A connector which is designed to accept a standard 0.062" printed circuit board. The contact pitch is 0.8 mm. The connector has ten contacts on each side. Both sides of the connector make contact to the same conductive element providing redundancy. nine conductive elements are used to detect the presence of moisture. The lamination is constructed such that the orientation of the electrode doesn't matter as long as it is properly seated in the connector. The unused conductive element is grounded.

In the illustrated embodiment, the connector is soldered on to secondary board. The secondary board is supported by a standoff mounted on the primary board. The standoff supports the secondary board at a fixed 1" distance above the primary board and thus locates the Wet/Dry Electrodes and the colocated Surface Temperature sensing element described herein.

In the illustrated embodiment, capacitors C5 through C13 provide DC isolation between the circuitry and the sensor surface. C14 and C15 are type NPO capacitors and are intended to provide a reference capacitance that may be used for temperature compensation. They are not used in the illustrated embodiment.

In the illustrated embodiment, connecting the sensing pins to external electrodes creates an electric field. The MC33794 generates a low frequency sine wave that is optimized for 120 KHz. The sine wave has very low harmonic content to reduce harmonic interference. The device supports nine electrodes that are driven and sensed sequentially under control of an external state machine. Pins 8 through 16 are used to drive the electrodes inserted into connector J1. Pins 31 through 34 are used to select the desired electrode according to the table shown in FIG. 9. The rectified, filtered and buffered signal is output on Pin 36 (LEVEL). LEVEL is connected to the input to Analog to Digital Converter that is part of the microcontroller U2. An external 2.5V Voltage Reference, U2 provides Microcontroller U2 with an accurate stable voltage source. Resistor R2 provides the proper bias current to U3 for stable and accurate operation. RS-485 Transceiver U4 provides for communications to a computer. The illustrated embodiment uses a 12-bit Analog to Digital Converter with the output left justified. The Wet/Dry values used in the illustrated embodiment reflect convention. In selected instances, the illustrated embodiment can yield good results with an 8-bit Analog to Digital Converter.

Not shown in the illustrated embodiment are the power supply circuits or other possible communications options such as RS-232, telephone or cellular modems, TCP/IP, other RF modems, and/or the like.

D. Conductivity Sensor

Figure 10:
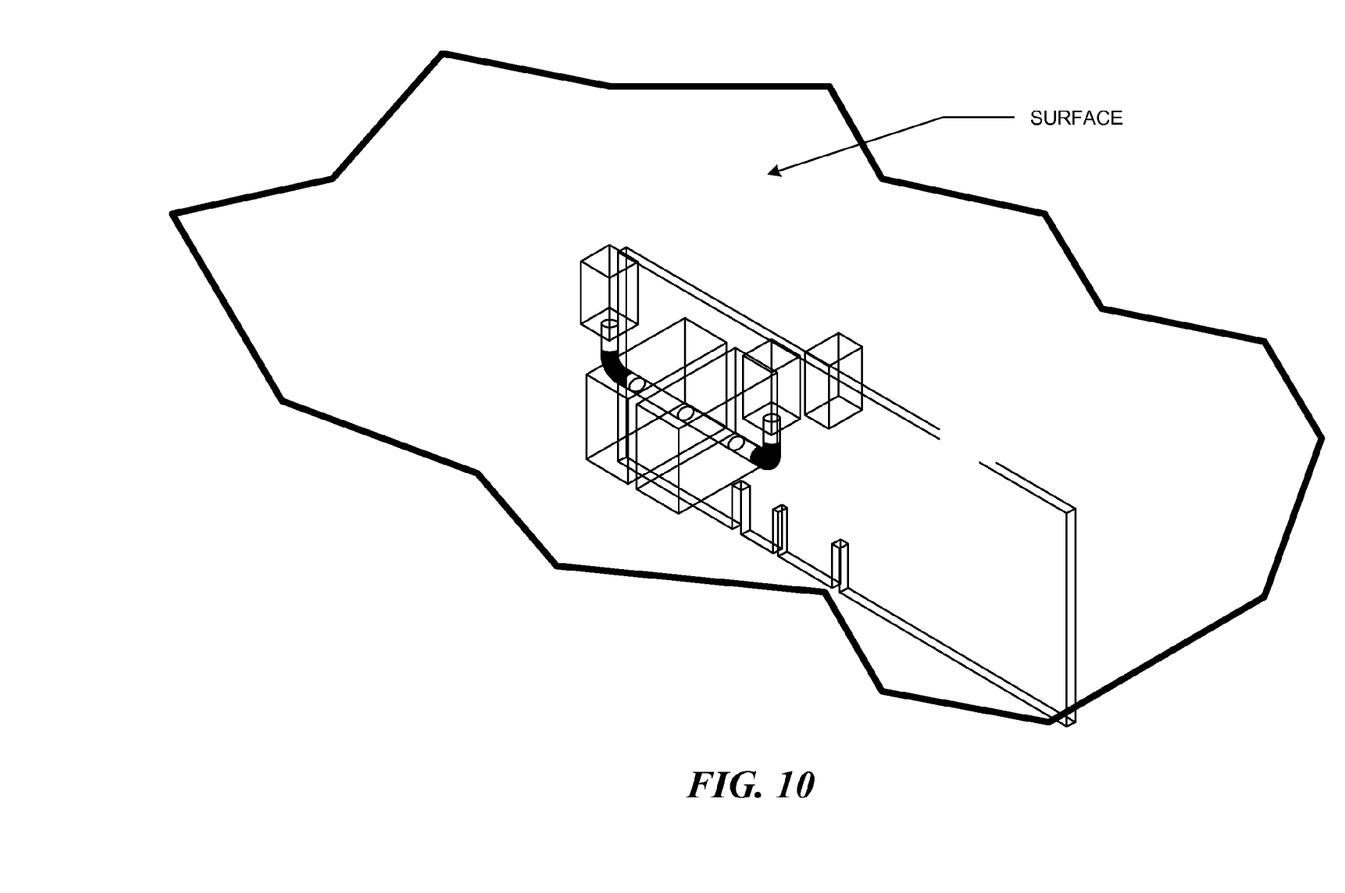
FIG. 10 is a partially schematic illustration of conductivity points and toroids in accordance with certain embodiments of the invention.
Figure 11:
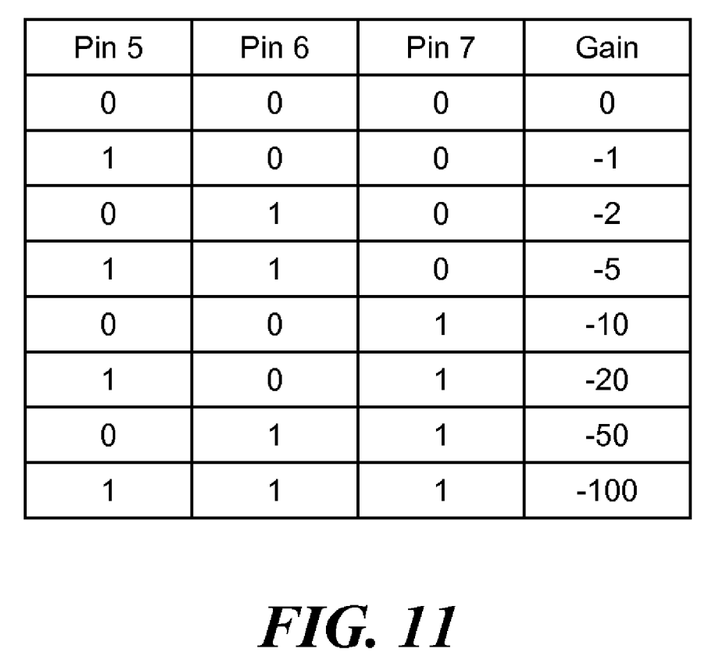
FIG. 11 is a table of programmable gain amplifier gain options in accordance with selected embodiments of the invention.
Figure 14:
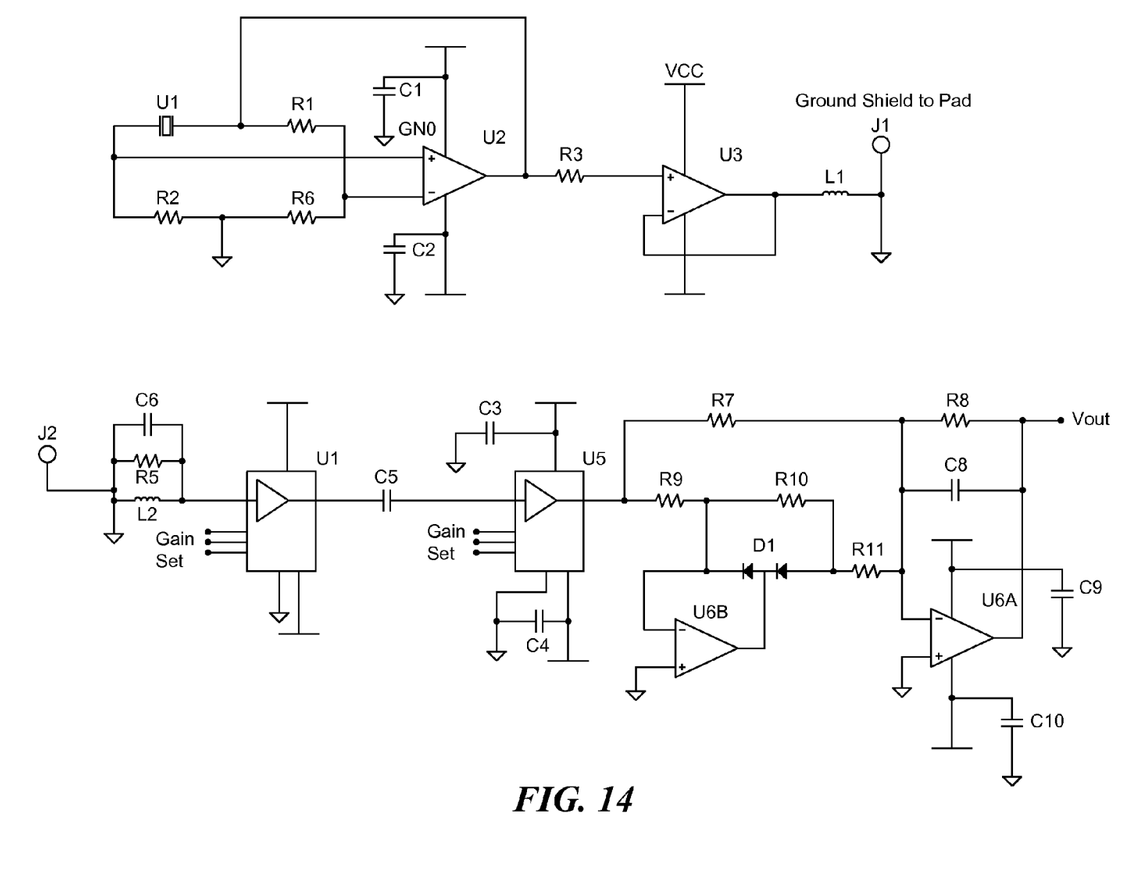
FIG. 14 is a partially schematic illustration of a conductivity sensor in accordance with certain embodiments of the invention.

A conductivity sensor in accordance with selected embodiments of the invention is discussed below with reference to FIGS. 10 and 14. In the illustrated embodiment, the conductivity sensor can include:

(1) An oscillator and driver circuits that drive Toroid C (L1 in FIG. 14). In the illustrated embodiment, both toroids are Renco Electronics RL3430 Current Sensors with 200 turns on the core and a frequency response from 1 to 100 KHz;
(2) A receiver toroid, Toroid D (L2 in FIG. 14);
(3) A precision rectifier and low pass filter (FIG. 14); and
(4) Electrodes (A & B) and wiring that allow the measurement of the surface conductance.

In the illustrated embodiment, toroids A & B are mounted side by side on a multilayer printed circuit board (PCB). One layer of the PCB is a ground plane. The toroids are enclosed in a five sided magnetic and capacitive shield made of 0.004" thick CO-NETIC AA foil manufactured by Magnetic Shield Corporation. Each shield is connected to a pad on the Printed Circuit Board (PCB) with a wire soldered to a via tied to the Ground plane. In selected embodiments, the shields (e.g., mumetal shields) can surround each toroid and can reduce or limit capacitive coupling and/or magnetic coupling between the toroids. In other embodiments, only one toroid or a selected number of toroids are surrounded by a shield.

In the illustrated embodiment, a crystal-controlled oscillator circuit is shown in the upper left hand corner of FIG. 14. In FIG. 14, the crystal-controlled oscillator has good stability over temperature and time. In the illustrated embodiment, the crystal, U1, has a frequency of 40 KHz. R2 and R6 provide switch point hysteresis with U1 providing positive feedback at the crystal's resonant frequency. Operational Amplifier (Op Amp) U2 provides the necessary gain to start and maintain oscillation. Resistor R3 provides isolation between the U2 and U3. In the illustrated embodiment, Op Amp U3 is configured as a unity gain buffer to prevent loading of the oscillator circuit and drives Toroid L1.

In the illustrated embodiment, electrode A is connected to Electrode B by a wire passing through the center of the toroids. The top side of Electrodes A and B are flush with the surface of the sensor and are exposed to whatever is present on the sensor's surface. When bare and dry, the sensor's surface can have an extremely high resistance and very little current will flow. When moisture is present, the resistance on the sensor surface can drop. For example, first order effects of the resistance drop can be caused by the amount and type of impurities present and the thickness of the moisture. When moisture freezes, the resistance can approach that of a bare and dry surface. When there is a conductive path across the sensor's surface, energy from toroid A is coupled to Toroid B.

In the illustrated embodiment, the signal detected by Toroid B is amplified by Amplifiers U4 and U5. U4 and U5 are Programmable Gain amplifiers. In the illustrated embodiment the use of an amplifier with integral gain set resistors can allow gain errors due to matching and thermal tracking of the gain resistors to be avoided. In the illustrated embodiment, the circuit requires very high gains to amplify the detected signal to a usable level and the use of discrete resistors could cause excessive gain errors that cannot be trimmed out or compensated for. In the illustrated embodiment, the amplifiers are inverting amplifiers and the polarity of the signal is inverted between the input and the output. In the illustrated embodiment, the gain of the circuit is changed dynamically to maintain the output signal in a range that has the least noise and most linear response. For example, in the illustrated embodiment, the gain is set by pins 5, 6, and 7 according to the table in FIG. 11.

In the illustrated embodiment, the output of U5 drives a classic precision rectifier and low pass filter circuit. For negative signals, the output of amplifier U6B is clamped to +0.7V by D1 pins 2 and 3 and disconnected from the summing point of U6A by D1 pins 1 and 3. U6A then functions as a simple unity-gain inverter with input resistor R7 and feedback resistor R8 giving a positive going output. For positive inputs, U6B operates as a normal amplifier connected to the summing point of U6A though resistor R11. Amplifier U6B then acts as a simple unity-gain inverter with input resistor R9 and feedback resistor R11. U6B gain accuracy is not affected by diode D1 pins 2 and 3 since the diode is inside the feedback loop. Positive current enters the U6A summing point though resistor R7 and negative current is drawn from the U6A summing point through resistor R11. Since the voltages across R7 and R11 are equal and opposite and R11 is one-half the value of R7, the net input current at the U6A summing point can be equal to and opposite from the current through R7 and amplifier U6A can operate as a summing inverter with unity gain, again giving a positive output. The circuit can become an averaging filter when C8 is connected across R8. The step response of this circuit is approximately 2 msec when the component values shown in FIG. 14 are used.

In the illustrated embodiment, the output, Vout, is sent to an Analog to Digital Converter. The output of the Analog to Digital converter is read by microcontroller. Algorithms are then used to determine the concentration of any liquid on the sensors surface based upon the conductivity sensor and the surface temperature.

Some of the embodiments of the invention discussed above can have one or more of the following advantages:

(1) Physical isolation of the electrodes from the detection electronics. There is no path for moisture to penetrate into the body of the sensor;
(2) There is no DC path to allow galvanic corrosion or electrode plating;
(3) There are no user adjustments required; and
(4) The packaging is very rugged.

E. Active and Passive Surface Sensor in One Package

In selected embodiments of the invention a passive sensor technology similar that described above with reference to the conductivity sensor can be combined with active sensor technology in a single package. For example, in certain embodiments a passive sensor technology or capability can be combined with an active sensor technology or capability, such as Peltier technology which actively modify the temperature of a portion of sensors surface in an attempt to freeze any moisture present and/or melt any ice present. By cooling the moisture present on the surface and detecting when it freezes the freeze point of the moisture can be determined. Alternatively, heat can be applied to existing ice to determine the conditions at which the ice melts or changes to water. In selected embodiments, when the presence of chemical(s) in the moisture or ice is known, the passive sensor technology can be used to determine the concentration of chemical(s) present by the conductivity reading and/or by the freeze point determination. However, contamination and the constituents of the freeze point depressant utilized can affect the accuracy of this process and the data obtained. In selected embodiments, using active sensor technology (e.g., using Peltier technology), the makeup of the moisture on the surface does not matter. The actual freeze point of the material or melting point of the material is determined. For example, this actual freeze point can account for the affect, or lack of effect, of any contaminants that could be present on the surface. In certain embodiments, accurate information on the surface and pavement temperatures combined with the freeze/melt point of the moisture or ice present on the surface can be used to determine the correct actions to take to maintain or regain a safe travel or other surfaces.

In selected embodiment the two sensor technologies are combined into a single encapsulated package with a single cable providing all communications to another component (e.g., an RPU). In certain embodiments, this approach can require less cutting of the surface it is being installed into/on, simplifying the installation process, reducing installation time, reducing installation costs and/or reducing installation materials. Additionally, in selected embodiments this approach can be less intrusive into the surface where it is to be installed and/or can reduce the chances of install failures do to the small number of separate components required to collect the data. Furthermore, in selected embodiments, the use of an embedded microcontoller, multiple temperature sensors, and active-passive intelligent sensor can provide the ability to utilize active sensor technology circuits without materially affecting the measurement of the surface temperature or the passive portion of the sensor package.

From the foregoing, it will be appreciated that specific embodiments of the invention have been described herein for purposes of illustration, but that various modifications may be made without deviating from the invention. For example, aspects of the invention described in the context of particular embodiments may be combined or eliminated in other embodiments. Although advantages associated with certain embodiments of the invention have been described in the context of those embodiments, other embodiments may also exhibit such advantages. Additionally, not all embodiments need necessarily exhibit such advantages to fall within the scope of the invention. Accordingly, the invention is not limited except as by the appended claims.

We claim:

1. A wet/dry sensing system for use in detecting a surface condition of a roadway surface, comprising:
   at least one driven electrode having a first surface substantially coplanar with the roadway surface and in communication with a roadway surface material;
   at least one grounded electrode adjacent to the driven electrode and having a second surface substantially coplanar with the roadway surface and in communication with the roadway surface material, wherein when the electrodes are driven by a sinusoidal signal between 10 KHz and 100 MHz either DC (Direct Current) or AC (Alternating Current) coupled between the electrodes, the driven signal is attenuated by any conductance of the roadway surface material between the at least one driven electrode and the at least one grounded electrode;
   a temperature sensor having at least a portion substantially adjacent to the roadway surface and configured to provide temperature data corresponding to a temperature of the roadway surface material; and
   a data processor coupled to the temperature sensor and one of the grounded electrode and the driven electrode, the data processor configured to use the attenuated signal and the temperature data for use in determining at least one of a presence of moisture on the roadway surface, a freezing point of moisture on the roadway surface, and the presence of ice on the roadway surface.

2. The system of claim 1, further comprising communication circuitry coupled to the data processor and configured to communicate with at least one of:
   a customer using text based open protocol;
   a Remote Processing Unit; and
   a Central Processing Unit.

3. The system of claim 2, further comprising communication circuitry configured to allow multiple sensors or nodes to reside on a communications bus.

4. The system of claim 2, further comprising communication circuitry configured to allow layered addressing method that allows one access point to customer's connection using master/slave communications.

5. The system of claim 1, further comprising communication circuitry configured to allow layered addressing method that allows one access point to customer's connection using master/slave communications.

6. The system claim 1 further comprising an oscillator connected to the at least one driven electrode and configured to provide the sinusoidal signal to the driven electrode.

7. The system of claim 1, further comprising a second grounded electrode with a third surface configured to be substantially coplanar with the roadway surface and in communication with the material on the roadway surface, the second grounded electrode being at least partially encapsulated with the at least one driven electrode and the at least one grounded electrode.

8. The system of claim 1, further comprising an encapsulant substantially encapsulating a portion of the at least one driven electrode, a portion of the at least one grounded electrode, and a portion of the temperature sensor for installation as a unit in the roadway with the first and second surfaces and the temperature sensor adjacent to the roadway surface and in communication with the roadway surface material.

* * * * *